United States Patent
Cowley

(10) Patent No.: US 11,413,058 B2
(45) Date of Patent: Aug. 16, 2022

(54) ULTRASONIC SURGICAL INSTRUMENT INCORPORATING CONTACTLESS TRANSFER OF DRIVE AND DATA SIGNALS

(71) Applicant: Covidien LP, Mansfield, MA (US)

(72) Inventor: Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 384 days.

(21) Appl. No.: 16/778,062

(22) Filed: Jan. 31, 2020

(65) Prior Publication Data
US 2020/0268407 A1    Aug. 27, 2020

Related U.S. Application Data

(60) Provisional application No. 62/809,005, filed on Feb. 22, 2019.

(51) Int. Cl.
*A61B 17/32* (2006.01)
*A61B 17/00* (2006.01)

(52) U.S. Cl.
CPC .............. *A61B 17/320068* (2013.01); *A61B 2017/00106* (2013.01); *A61B 2017/00221* (2013.01); *A61B 2017/00734* (2013.01)

(58) Field of Classification Search
CPC .. A61B 17/320068; A61B 2017/00106; A61B 2017/00221; A61B 2017/00734
See application file for complete search history.

(56) References Cited

U.S. PATENT DOCUMENTS

| | | | |
|---|---|---|---|
| 8,435,257 B2 | 5/2013 | Smith et al. | |
| 2004/0116952 A1 | 6/2004 | Sakurai et al. | |
| 2013/0274732 A1 | 10/2013 | Wiener et al. | |
| 2014/0207124 A1 | 7/2014 | Aldridge et al. | |
| 2015/0088115 A1 | 3/2015 | Smith | |
| 2017/0245880 A1 | 8/2017 | Honda et al. | |

*Primary Examiner* — Ashley L Fishback
(74) *Attorney, Agent, or Firm* — Carter, DeLuca & Farrell LLP

(57) ABSTRACT

An ultrasonic surgical instrument includes a handle assembly, a waveguide extending distally therefrom to an end effector, an ultrasonic transducer assembly supported by the handle assembly, and a drive signal antenna. The ultrasonic transducer assembly includes a transducer, a horn extending distally from the transducer, an electrode antenna disposed about and operably coupled to the transducer, and an outer casing enclosing the transducer, the electrode antenna, and a portion of the horn. Another portion of the horn extends distally from the outer casing to operably connect to the waveguide. The drive signal antenna is disposed externally of and adjacent to the ultrasonic transducer assembly and is configured to contactlessly transmit a drive signal through the outer casing to the electrode antenna to thereby energize the transducer such that ultrasonic energy is transmitted from the horn along the waveguide to the end effector for treating tissue therewith.

20 Claims, 3 Drawing Sheets

ULTRASONIC SURGICAL INSTRUMENT INCORPORATING CONTACTLESS TRANSFER OF DRIVE AND DATA SIGNALS

CROSS-REFERENCE TO RELATED APPLICATIONS

This application claims the benefit of and priority to U.S. Provisional Patent Application Ser. No. 62/809,005 filed Feb. 22, 2019, the entire disclosure of which is incorporated by reference herein.

BACKGROUND

Technical Field

The present disclosure relates to ultrasonic surgical instruments and, more particularly, to an ultrasonic surgical instrument incorporating contactless transfer of drive and/or data signals between a generator assembly and transducer assembly thereof.

Background of Related Art

Ultrasonic surgical instruments utilize mechanical vibration energy transmitted at ultrasonic frequencies to treat, e.g., dissect, coagulate, cauterize, fuse, seal, cut, desiccate, and/or fulgurate, tissue.

Ultrasonic surgical instruments typically employ a transducer coupled to a handle of the ultrasonic surgical instrument and configured to produce ultrasonic energy for transmission along a waveguide to an end effector of the ultrasonic surgical instrument that is designed to treat tissue with the ultrasonic energy. The transducer may be driven by an ultrasonic generator that is on-board, e.g., on or within the handle of the ultrasonic surgical instrument, or remotely disposed, e.g., as a set-top box connected to the ultrasonic surgical instrument via a surgical cable. The end effector of the ultrasonic surgical instrument may include a blade that receives the ultrasonic energy from the waveguide for application to tissue and a jaw member configured to clamp tissue between the blade and the jaw member to facilitate treatment thereof.

SUMMARY

As used herein, the term "distal" refers to the portion that is described which is further from a user, while the term "proximal" refers to the portion that is being described which is closer to a user. Further, any or all of the aspects detailed herein, to the extent consistent, may be used in conjunction with any or all of the other aspects detailed herein.

Provided in accordance with aspects of the present disclosure is an ultrasonic surgical instrument including a handle assembly, a waveguide extending distally from the handle assembly to an end effector configured to treat tissue, an ultrasonic transducer assembly supported by the handle assembly, and a drive signal antenna. The ultrasonic transducer assembly including an ultrasonic transducer, an ultrasonic horn extending distally from the ultrasonic transducer, an electrode antenna disposed about and operably coupled to the ultrasonic transducer, and an outer casing enclosing the ultrasonic transducer, the electrode antenna, and a first portion of the ultrasonic horn. A second portion of the ultrasonic horn extends distally from the outer casing to operably connect to the waveguide. The drive signal antenna is disposed externally of and adjacent to the outer casing of the ultrasonic transducer assembly. The drive signal antenna is configured to contactlessly transmit a drive signal through the outer casing to the electrode antenna to thereby energize the ultrasonic transducer such that ultrasonic energy is transmitted from the ultrasonic horn along the waveguide to the end effector for treating tissue therewith.

In an aspect of the present disclosure, the drive signal antenna is disposed within the handle assembly.

In another aspect of the present disclosure, a generator assembly is supported by the handle assembly. The generator assembly, in such aspects, includes the drive signal antenna. A battery assembly is also supported by the handle assembly and configured to power the generator assembly.

In another aspect of the present disclosure, the generator assembly and the ultrasonic transducer assembly are coupled to one another and are together selectively removable from the handle assembly.

In yet another aspect of the present disclosure, the generator assembly further includes drive signal generating circuitry configured to generate the drive signal and transmit the drive signal to the drive signal antenna for contactless transmission to the electrode antenna.

In still another aspect of the present disclosure, the generator assembly further includes power receiving circuitry configured to receive power from the battery assembly to generate the drive signal. In aspects, the power is a DC signal and the drive signal is an AC signal.

In still yet another aspect of the present disclosure, the electrode antenna is disposed annularly about the ultrasonic transducer to enable contactlessly transmission of the drive signal thereto in any rotational orientation of the ultrasonic transducer assembly relative to the drive signal antenna.

In another aspect of the present disclosure, the ultrasonic transducer assembly further includes a data chip associated with an antenna of the ultrasonic transducer assembly to enable contactless transmission of data from the data chip through the outer casing to an external antenna. The antenna associated with the data chip may be a data signal antenna or the electrode antenna. The external antenna may be the drive signal antenna or a data signal antenna. Regardless of the antenna configuration, the data may be at least one of stored data or sensed data.

Another ultrasonic surgical instrument provided in accordance with aspects of the present disclosure includes a handle assembly, a waveguide extending distally from the handle assembly to an end effector configured to treat tissue, an ultrasonic transducer assembly supported by the handle assembly, and a generator assembly supported by the handle assembly. The ultrasonic transducer assembly includes an ultrasonic transducer, an ultrasonic horn extending distally from the ultrasonic transducer, an electrode antenna disposed about and operably coupled to the ultrasonic transducer, and an outer casing enclosing the ultrasonic transducer, the electrode antenna, and a first portion of the ultrasonic horn. A second portion of the ultrasonic horn extends distally from the outer casing to operably connect to the waveguide. The generator assembly includes drive signal generating circuitry and a drive signal antenna. The drive signal generating circuitry is configured to generate a drive signal and transmit the drive signal to the drive signal antenna for contactless transmission of the drive signal through the outer casing to the electrode antenna to thereby energize the ultrasonic transducer such that ultrasonic energy is transmitted from the ultrasonic horn along the waveguide to the end effector for treating tissue therewith.

In an aspect of the present disclosure, a battery assembly is supported by the handle assembly and configured to power the generator assembly. In such aspects, the generator assembly further includes power receiving circuitry configured to receive power from the battery assembly. The power received may be a DC signal while the drive signal is an AC signal.

In another aspect of the present disclosure, the generator assembly and the ultrasonic transducer assembly are coupled to one another and are together selectively removable from the handle assembly.

In yet another aspect of the present disclosure, the ultrasonic transducer assembly is rotatable relative to the generator assembly. In such aspects, the electrode antenna is disposed annularly about the ultrasonic transducer to enable contactlessly transmission of the drive signal thereto in any rotational orientation of the ultrasonic transducer assembly relative to the generator assembly.

In still another aspect of the present disclosure, the ultrasonic transducer assembly further includes a data chip associated with an antenna of the ultrasonic transducer assembly to enable contactless transmission of data from the data chip through the outer casing to an antenna associated with the generator assembly.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
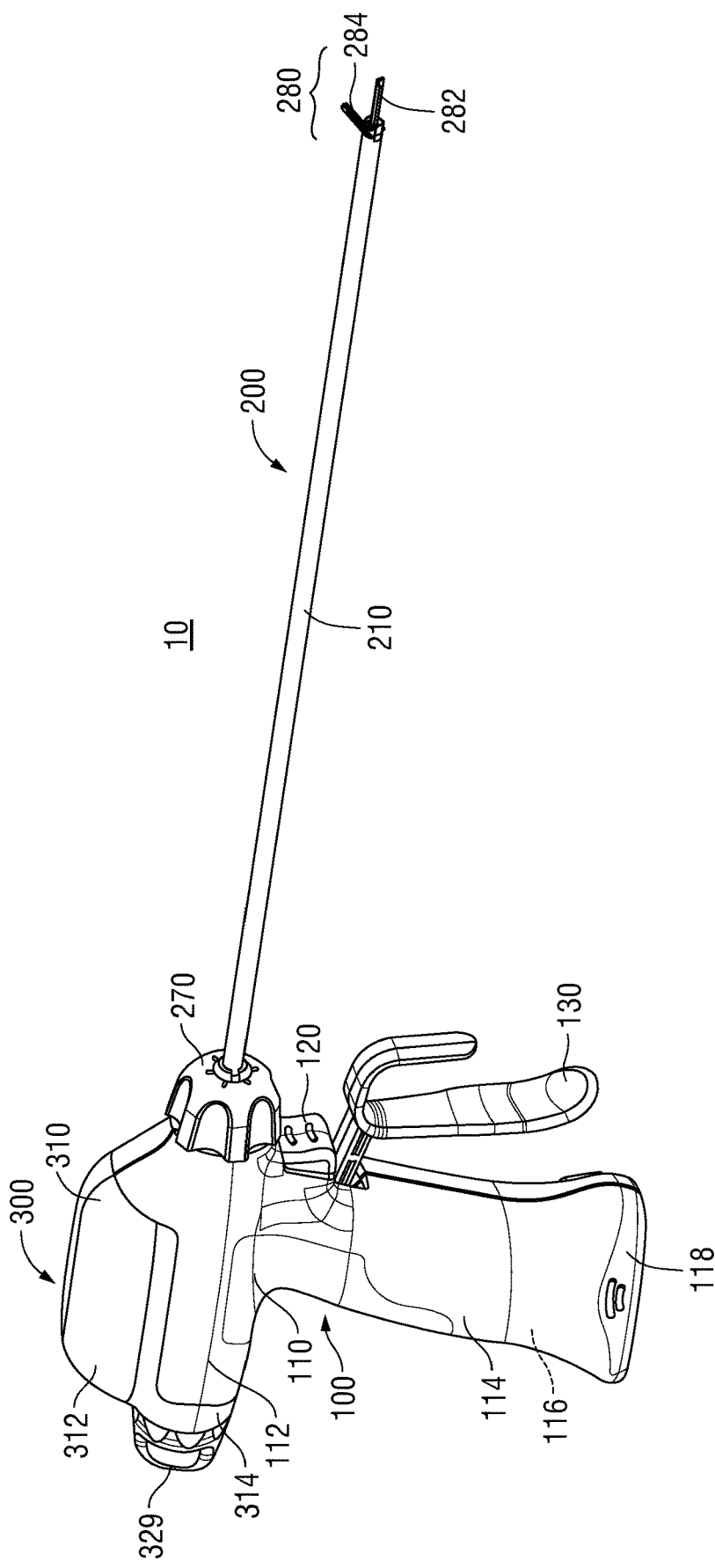
FIG. 1 is a side, perspective view of an ultrasonic surgical instrument provided in accordance with the present disclosure.
Figure 2:
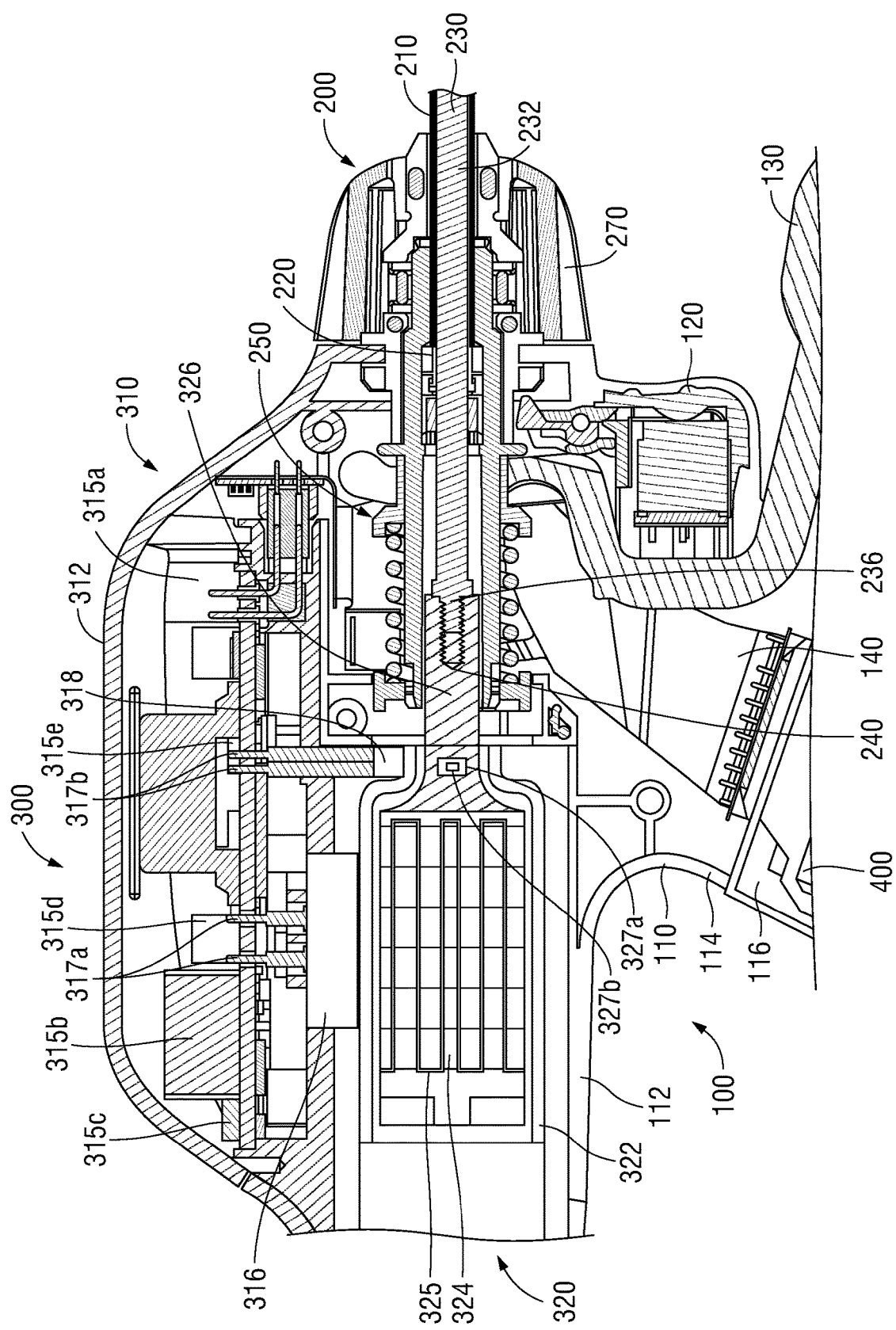
FIG. 2 is an enlarged, side, longitudinal, cross-sectional view of a proximal portion of the ultrasonic surgical instrument of FIG. 1.

Referring to FIGS. 1 and 2, an ultrasonic surgical instrument 10 provided in accordance with the present disclosure includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support an ultrasonic transducer and generator assembly ("TAG") 300 including a generator assembly 310 and an ultrasonic transducer assembly 320. TAG 300 may be permanently engaged with body portion 112 of housing 110 or removable therefrom. Generator assembly 310 and ultrasonic transducer assembly 320 may be permanently coupled with one another, may be removably coupled with one another, or may separately and independently couple to housing 110. Generator assembly 310 includes an outer housing 312 configured to house the internal electronics of generator assembly 310, and a cradle 314 configured to rotatably support ultrasonic transducer assembly 320.

The internal electronics of generator assembly 310 include power receiving circuitry 315a, a microprocessor 315b, a memory 315c, drive signal generating circuitry 315d, and communication circuitry 315e. Drive signal generating circuitry 315d is operably coupled with a drive signal antenna 316 of generator assembly 310, e.g., via electrical wires 317a, while communication circuitry 315e is operably coupled with a data signal antenna 318 of generator assembly 310, e.g., via electrical wires 317b. Power receiving circuitry 315a of generator assembly 310 is configured to receive a suitable power signal, e.g., a DC power signal from battery assembly 400, and transmit the same to drive signal generating circuitry 315d which, as controlled by microprocessor 315b, converts the DC power signal into a high voltage AC waveform drive signal configured to drive a piezoelectric stack 324 of ultrasonic transducer assembly 320. The drive signal is configured to be output from drive signal generating circuitry 315d to drive signal antenna 316 via electrical wires 317a and drive signal antenna 316 is configured to contactlessly transmit the drive signal to ultrasonic transducer assembly 320, as detailed below.

Communication circuitry 315e is configured to receive data signals from data signal antenna 318 via electrical wires 317b. Data signal antenna 318, more specifically, receives data signals from ultrasonic transducer assembly 320 in a contactless fashion, as detailed below, and transmits the same to communication circuitry 315e. Communication circuitry 315e may transmit the received data signals to memory 315c for storage therein, and/or to microprocessor 315b, drive signal generating circuitry 315d, or other suitable components of generator assembly 310 to facilitate feedback-based control of the drive signal or other setting.

Continuing with reference to FIGS. 1 and 2, ultrasonic transducer assembly 320 includes an outer casing 322, a piezoelectric stack 324, an electrode antenna 325 operably coupled to piezoelectric stack 324, an ultrasonic horn 326 extending distally from piezoelectric stack 324, a data chip 327a incorporating a data antenna 327b and disposed on ultrasonic horn 326 (although other locations are also contemplated), and a bolt 328 securing piezoelectric stack 324 between horn 326 and a proximal nut (not shown). Outer casing 322 defines a rotation knob 329 (FIG. 1) at a proximal end portion thereof. In embodiments, outer casing 3223 is formed from a suitable polymeric material capable of withstanding sterilization.

Electrode antenna 325, more specifically, defines a generally cylindrical configuration that is disposed annularly about piezoelectric stack 324, e.g., extending 360 degrees about piezoelectric stack 324. At least one positive electrode and at least one negative electrode of the piezoelectric stack 324 are disposed between the piezoelectric elements that form the piezoelectric stack 324 and electrically coupled to the electrode antenna 325. As such, a voltage may be applied across the piezoelectric elements via the positive and negative electrodes. The piezoelectric stack 324, in turn, converts the applied voltage into mechanical energy, in the form of ultrasonic vibrations, that is transmitted to ultrasonic horn 326.

Data chip 327a, more specifically, may be a microprocessor chip or other suitable chip with sensory circuitry to detect various conditions, parameters, properties, etc. of piezoelectric stack 324, ultrasonic horn 326, and/or other portions of ultrasonic transducer assembly 320. Data chip 327a is configured to sense, for example, a frequency, amplitude, impedance, and/or temperature of ultrasonic horn 326 (or other portion of ultrasonic transducer assembly 320); the number of times ultrasonic transducer assembly 320 has been activated, the duration of activation ultrasonic transducer assembly 320, etc. Data chip 327a may additionally or alternatively include a memory storing information relating to ultrasonic transducer assembly 320 such as, for example, model, serial number, manufacture date, calibration and/or testing information, manufacturer setting information, etc. In embodiments where data chip 327a includes sensor circuitry, the memory may also store the sensed data. Data antenna 327b is incorporated into or operably coupled with data chip 327a to enable communication of data signals therebetween. In embodiments, electrode antenna 325 and drive signal antenna 316 allows for transmission of both drive and data signals and, thus, in such embodiments, data antenna 327b of chip 327a and data signal antenna 318 need not be provided.

Outer casing 322 of ultrasonic transducer assembly 320, as noted above, includes rotation knob 329 at a proximal end portion thereof. The body of outer casing 322 and rotation knob 329 may be monolithically formed, engaged, or otherwise secured with one another to define outer casing 322. Outer casing 322 forms an enclosure that encapsulates the proximal nut, piezoelectric stack 324, electrode antenna 325, a proximal portion of ultrasonic horn 326, data chip and antenna 327a, 327b, and bolt 328. A distal portion of ultrasonic horn 326 extends distally from outer casing 322 to enable connection with waveguide 230, as detailed below.

The enclosure formed via outer casing 322 may be hermetically sealed to inhibit fluids, contaminants, debris, etc. from entering the enclosure and to enable sterilization of ultrasonic transducer assembly 320 in preparation for repeated use. Further, as contactless drive and data signals are transmitted between generator assembly 310 and ultrasonic transducer assembly 320, as detailed below, outer casing 322 need not include any electrical wires, contacts, or other conductors extending therethrough. Obviating the need for electrical wires, contacts, or other conductors extending through outer casing 322 helps eliminate seams in the enclosure, thus providing a more robust hermetic seal.

Rotation knob 329 is accessible from the exterior of handle assembly 100 (FIG. 1) and is configured for manual rotation to rotate ultrasonic transducer assembly 320 relative to generator assembly 310 and housing 110, e.g., to facilitate engagement of ultrasonic transducer assembly 320 with waveguide 230 of elongated assembly 200 and/or rotation of ultrasonic transducer assembly 320 and elongated assembly 200 relative to generator assembly 310 and housing 110 to orient end effector 280 of elongated assembly 200 (see FIG. 1) in a desired orientation.

Referring still to FIGS. 1 and 2, fixed handle portion 114 of housing 110 defines a compartment 116 configured to receive a battery assembly 400 and a door 118 configured to enclose compartment 116. An electrical connection assembly 140, e.g., a flex circuit, is disposed within housing 110 of handle assembly 100 and serves to electrically couple activation button 120, power receiving circuitry 315a of generator assembly 310 of TAG 300, and battery assembly 400 with one another when TAG 300 is supported on or within body portion 112 of housing 110 and battery assembly 400 is disposed within compartment 116 of fixed handle portion 114 of housing 110, thus enabling activation of TAG 300 in response to depression of activation button 120.

Elongated assembly 200 of ultrasonic surgical instrument 10 includes an outer drive sleeve 210, an inner support sleeve 220 disposed within outer drive sleeve 210, a waveguide 230 extending through inner support sleeve 220, a drive assembly 250, a rotation knob 270, and an end effector 280 including a blade 282 and a jaw 284. A proximal portion of outer drive sleeve 210 is operably coupled to clamp trigger 130 of handle assembly 100 via drive assembly 250, while a distal portion of outer drive sleeve 210 is operably coupled to jaw 284. As such, clamp trigger 130 is selectively actuatable to thereby move outer drive sleeve 210 about inner support sleeve 220 to pivot jaw 284 relative to blade 282 of end effector 280 from a spaced-apart position to an approximated position for clamping tissue between jaw 284 and blade 282. Drive assembly 250 provides a force-limiting feature whereby the clamping pressure applied to tissue is limited to a particular clamping pressure or particular clamping pressure range. Rotation knob 270 is rotatable in either direction to rotate elongated assembly 200 in either direction relative to handle assembly 100.

Waveguide 230, as noted above, extends through inner support sleeve 220. Waveguide 230 defines a body 232 and a blade 282 extending from the distal end of body 232. Blade 282 serves as the blade of end effector 280. Waveguide 230 further includes a proximal connector 236, e.g., a threaded male connector, configured for threaded engagement within a connector 340 of ultrasonic horn 326, e.g., a threaded female receiver, such that ultrasonic motion produced by ultrasonic transducer assembly 320 is transmitted from ultrasonic horn 326, along waveguide 230 to blade 282 for treating tissue clamping between blade 282 and jaw 284 or positioned adjacent to blade 282.

Figure 3:
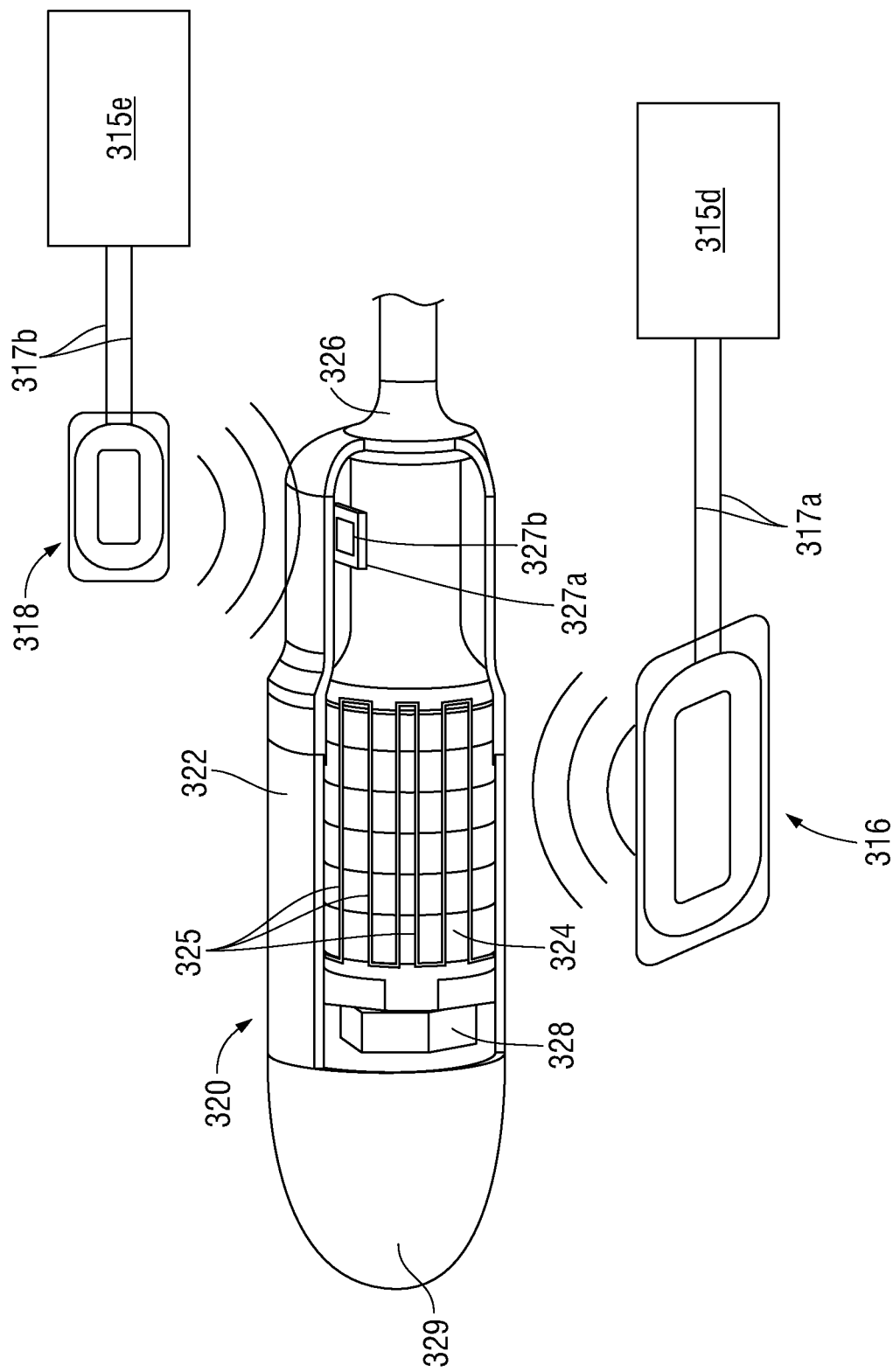
FIG. 3 is a schematic representation illustrating contactless transfer of drive and data signals between generator and ultrasonic transducer assemblies of the ultrasonic surgical instrument of FIG. 1.

Referring to FIG. 3, in conjunction with FIGS. 1 and 2, drive signal antenna 316 of generator assembly 310 is configured to contactlessly transmit the high voltage AC waveform drive signal produced by drive signal generating circuitry 315d to electrode antenna 325 of ultrasonic transducer assembly 320. The antennas 316, 325 may be configured to contactlessly transmit and receive, respectively, the drive signal through outer casing 322 of ultrasonic transducer assembly 320 via the use of radio waves, magnetic resonance coupling, acoustics, or other suitable contactless energy transmission method. Due to the fact that electrode antenna 325 is annularly disposed, the drive signal is capable of being transmitted from antenna 316 to antenna 325 in any rotational orientation of ultrasonic transducer assembly 320 relative to generator assembly 310. Further, as the drive signal is transmitted contactlessly, the need for brush, slip ring, or other rotational drive contact components is obviated, eliminating the costs and shorting potential associated therewith in addition to, as noted above, the elimination of the need for seams or breaks in outer casing 322.

Data antenna 327b of data chip 327a of ultrasonic transducer assembly 320 is configured to contactlessly transmit data from data chip 327a to data signal antenna 318 of generator assembly 310. Antennas 327b, 318 may be configured to contactlessly transmit and receive data through outer casing 322 of ultrasonic transducer assembly 320 via the use of radio waves (using RFID, near-field communication, etc.), microwaves, IR, or other suitable contactless data transmission method. Antenna 327b may be configured to extend annually about ultrasonic transducer assembly 320 to enable data communication in any orientation, similarly as detailed above with respect to antenna 325, although other configurations are also contemplated. Further, as data is transmitted contactlessly, the need for brush, slip ring, or other rotational data contact components is obviated, eliminating the costs and shorting potential associated therewith and also eliminating, as noted above, the need for seams or breaks in outer casing 322.

Turning back to FIGS. 1 and 2, although ultrasonic surgical instrument 10 is detailed hereinabove as including generator assembly 310 and battery assembly 400 on or within handle assembly 100, it is also contemplated that ultrasonic surgical instrument 10 be configured to connect to a remote generator and power source via a surgical cable. In such embodiments, the contactless drive signal and data signal communication between generator assembly 310 and ultrasonic transducer assembly 320 would remain similar as detailed above except that drive signal antenna 316 and data signal antenna 318 would be re-located to handle assembly 100 (rather than the generator) to be positioned adjacent ultrasonic transducer assembly 320 (similarly as illustrated in FIG. 2), and connected to the drive signal generating circuitry and communication circuitry of the remote generator via elongated electrical wires extending through the surgical cable. In such embodiments, an on-board battery (not shown) may be provided on or within handle assembly 100 to power, for example, drive signal antenna 316 and data signal antenna 318. Alternatively or additionally, the drive signal generating circuitry and/or communication circuitry may remain on or within handle assembly 100 and powered by the on-board battery or powered by the remote generator via the surgical cable. That is, any suitable combination of on-board and/or remote components is contemplated.

It is further contemplated that ultrasonic surgical instrument 10 be configured with ultrasonic transducer assembly 320 disposed in a distal location such as, for example, distally of an articulating section of elongated assembly 200, with waveguide 230 extending a relatively shorter distance from ultrasonic transducer assembly 320 to end effector 280. In such embodiments, the contactless drive signal and data signal communication between generator assembly 310 and ultrasonic transducer assembly 320 would remain similar as detailed above except that drive signal antenna 316 and data signal antenna 318 would be re-located to a position adjacent the ultrasonic transducer assembly 320 with elongated electrical wires extending through elongated assembly 200 to connect to generator assembly 310 at handle assembly 100 (or further extending through a surgical cable to connect to a remote generator). In such embodiments, the manual features of handle assembly 100 may be eliminated and handle assembly 100 may instead be configured as an attachment housing configured for operably attachment to a surgical robot. Handle assembly 100 may likewise be configured as an attachment housing configured for operably attachment to a surgical robot in embodiments where ultrasonic transducer assembly 320 is more proximally-positioned, e.g., on or within handle assembly 100.

Referring generally to FIGS. 1-3, in use, ultrasonic instrument 10 is advanced into a surgical site and manipulated, e.g., end effector 280 is rotated via rotation of rotation knob 329 and/or rotation knob 270, such that end effector 280 is positioned with tissue to be treated disposed between jaw 284 and blade 282 with jaw 284 disposed in the open position (FIG. 1). Thereafter, clamp trigger 130 is squeezed towards fixed handle portion 114 of housing 110 from an un-actuated position to an actuated position to translate outer drive sleeve 210 about inner support sleeve 220 and relative to end effector 280, thereby pivoting jaw 284 relative to blade 282 from the open position towards a clamped position to clamp tissue between jaw 284 and blade 282.

With tissue clamped in the manner detailed above, blade 282 may be activated, e.g., via depression of activation button 120. Upon depression of activation button 120, a DC power signal is supplied from battery assembly 400 to power receiving circuitry 315*a* of generator assembly 310; drive signal generating circuitry 315*d* of generator assembly 310, controlled by microprocessor 315*b*, converts the DC power signal into a high voltage AC waveform drive signal; the drive signal is transmitted to drive signal antenna 316 via electrical wires 317*a*; drive signal antenna 316 contactlessly transmits the drive signal to electrode antenna 325 of ultrasonic transducer assembly 320; and piezoelectric stack 324 is activated by the drive signal. Activation of piezoelectric stack 324 produces ultrasonic energy that is transmitted to ultrasonic horn 326, along waveguide 230, and to blade 282. The ultrasonic energy provided at blade 282 is used to heat and, ultimately, treat, e.g., seal, tissue clamped between jaw 284 and blade 282. Blade 282 may also be energized, in the manner detailed above, and moved relative to tissue to treat, e.g., dissect, tissue without clamping tissue between jaw 284 and blade 282.

During, before, and/or after use, data collected by data chip 327*a* may be transmitted to data antenna 327*b* for contactless transmission from data antenna 327*b* of ultrasonic transducer assembly 320 to data signal antenna 318 of generator assembly 310. Data signal antenna 318 transmits the data to communication circuitry 315*e* of generator assembly 310 for storage in memory 315*c* and/or use in feedback-based control of the drive signal and/or other suitable settings.

While several embodiments of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
   a handle assembly;
   a waveguide extending distally from the handle assembly to an end effector configured to treat tissue;
   an ultrasonic transducer assembly supported by the handle assembly, the ultrasonic transducer assembly including an ultrasonic transducer, an ultrasonic horn extending distally from the ultrasonic transducer, an electrode antenna disposed about and operably coupled to the ultrasonic transducer, and an outer casing enclosing the ultrasonic transducer, the electrode antenna, and a first portion of the ultrasonic horn, wherein a second portion of the ultrasonic horn extends distally from the outer casing to operably connect to the waveguide; and
   a drive signal antenna disposed externally of and adjacent to the outer casing of the ultrasonic transducer assembly, wherein the drive signal antenna is configured to contactlessly transmit a drive signal through the outer casing to the electrode antenna to thereby energize the ultrasonic transducer such that ultrasonic energy is transmitted from the ultrasonic horn along the waveguide to the end effector for treating tissue therewith.

2. The ultrasonic surgical instrument according to claim 1, wherein the drive signal antenna is disposed within the handle assembly.

3. The ultrasonic surgical instrument according to claim 1, further comprising:
   a generator assembly supported by the handle assembly, wherein the generator assembly includes the drive signal antenna; and
   a battery assembly supported by the handle assembly, wherein the battery assembly is configured to power the generator assembly.

4. The ultrasonic surgical instrument according to claim 3, wherein the generator assembly and the ultrasonic transducer assembly are coupled to one another and are together selectively removable from the handle assembly.

5. The ultrasonic surgical instrument according to claim 3, wherein the generator assembly further includes drive signal generating circuitry configured to generate the drive signal and transmit the drive signal to the drive signal antenna for contactless transmission to the electrode antenna.

6. The ultrasonic surgical instrument according to claim 5, wherein the generator assembly further includes power receiving circuitry configured to receive power from the battery assembly to generate the drive signal.

7. The ultrasonic surgical instrument according to claim 6, wherein the power is a DC signal and wherein the drive signal is an AC signal.

8. The ultrasonic surgical instrument according to claim 1, wherein the electrode antenna is disposed annularly about the ultrasonic transducer to enable contactless transmission of the drive signal thereto in any rotational orientation of the ultrasonic transducer assembly relative to the drive signal antenna.

9. The ultrasonic surgical instrument according to claim 1, wherein the ultrasonic transducer assembly further includes a data chip associated with an antenna of the ultrasonic transducer assembly to enable contactless transmission of data from the data chip through the outer casing to an external antenna.

10. The ultrasonic surgical instrument according to claim 9, wherein the antenna associated with the data chip is a data signal antenna.

11. The ultrasonic surgical instrument according to claim 9, wherein the antenna associated with the data chip is the electrode antenna and the external antenna is the drive signal antenna such that the electrode antenna and the external antenna are configured to contactlessly transmit both the drive signal and the data.

12. The ultrasonic surgical instrument according to claim 9, wherein the data is at least one of stored data or sensed data.

13. An ultrasonic surgical instrument, comprising:
a handle assembly;
a waveguide extending distally from the handle assembly to an end effector configured to treat tissue;
an ultrasonic transducer assembly supported by the handle assembly, the ultrasonic transducer assembly including an ultrasonic transducer, an ultrasonic horn extending distally from the ultrasonic transducer, an electrode antenna disposed about and operably coupled to the ultrasonic transducer, and an outer casing enclosing the ultrasonic transducer, the electrode antenna, and a first portion of the ultrasonic horn, wherein a second portion of the ultrasonic horn extends distally from the outer casing to operably connect to the waveguide; and
a generator assembly supported by the handle assembly, the generator assembly including drive signal generating circuitry and a drive signal antenna, wherein the drive signal generating circuitry is configured to generate a drive signal and transmit the drive signal to the drive signal antenna for contactless transmission of the drive signal through the outer casing to the electrode antenna to thereby energize the ultrasonic transducer such that ultrasonic energy is transmitted from the ultrasonic horn along the waveguide to the end effector for treating tissue therewith.

14. The ultrasonic surgical instrument according to claim 13, further comprising a battery assembly supported by the handle assembly, wherein the battery assembly is configured to power the generator assembly.

15. The ultrasonic surgical instrument according to claim 14, wherein the generator assembly further includes power receiving circuitry configured to receive power from the battery assembly.

16. The ultrasonic surgical instrument according to claim 15, wherein the power received is a DC signal and wherein the drive signal is an AC signal.

17. The ultrasonic surgical instrument according to claim 13, wherein the generator assembly and the ultrasonic transducer assembly are coupled to one another and are together selectively removable from the handle assembly.

18. The ultrasonic surgical instrument according to claim 13, wherein the ultrasonic transducer assembly is rotatable relative to the generator assembly.

19. The ultrasonic surgical instrument according to claim 18, wherein the electrode antenna is disposed annularly about the ultrasonic transducer to enable contactless transmission of the drive signal thereto in any rotational orientation of the ultrasonic transducer assembly relative to the generator assembly.

20. The ultrasonic surgical instrument according to claim 13, wherein the ultrasonic transducer assembly further includes a data chip associated with an antenna of the ultrasonic transducer assembly to enable contactless transmission of data from the data chip through the outer casing to an antenna associated with the generator assembly.

* * * * *